United States Patent
Rockwood, Jr. et al.

(10) Patent No.: US 7,160,328 B2
(45) Date of Patent: *Jan. 9, 2007

(54) METHOD FOR SECURING A GLENOID COMPONENT TO A SCAPULA

(75) Inventors: Charles A. Rockwood, Jr., San Antonio, TX (US); Michael A. Wirth, San Antonio, TX (US); Thomas S. Camino, Warsaw, IN (US); Jack F. Long, Warsaw, IN (US); Jeffrey M. Ondrla, Leesburg, IN (US)

(73) Assignee: DePuty Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/129,966

(22) Filed: May 16, 2005

(65) Prior Publication Data

US 2005/0209700 A1 Sep. 22, 2005

Related U.S. Application Data

(63) Continuation of application No. 09/802,150, filed on Mar. 8, 2001, now Pat. No. 6,911,047.

(60) Provisional application No. 60/190,391, filed on Mar. 17, 2000.

(51) Int. Cl.
*A61F 2/28* (2006.01)
*A61B 19/00* (2006.01)

(52) U.S. Cl. ............... 623/19.13; 623/19.11; 128/898

(58) Field of Classification Search .. 623/19.11–19.14, 623/20.14, 20.34, 20.36, 20.18, 21.15–21.19; 606/72, 73, 86, 87

See application file for complete search history.

(56) References Cited

U.S. PATENT DOCUMENTS 3,252,677 A 5/1966 Raymond (Continued)

FOREIGN PATENT DOCUMENTS

EP 0 151 724 12/1984

(Continued)

OTHER PUBLICATIONS

Cementless Fixation: Using a Polyethylene Oseo-Integration PEG as used on the Freeman-Samuelson Knee brochure, produced by Finsbury Instruments Limited London in conjunction with Adrian Tuke Limited, 1982.

(Continued)

*Primary Examiner*—David J. Isabella
(74) *Attorney, Agent, or Firm*—Maginot, Moore & Beck (57) ABSTRACT

A medical procedure includes providing a prosthesis which includes (i) a body portion having a rear surface and a bearing surface, and (ii) an anchor peg including a shaft extending from the rear surface of the body portion, wherein the anchor peg includes a plurality of outwardly extending fins secured to the shaft, and further wherein the plurality of outwardly extending fins each possesses a first diameter. The medical procedure further includes creating an anchor hole in a natural bone, the anchor hole possessing a second diameter which is less than the first diameter. In addition, the method procedure includes positioning the anchor peg within the anchor hole so that each of the plurality of outwardly extending fins deforms so as to possess (i) a concave side which faces an open end of the anchor hole, and (ii) a convex side that faces a closed end of the anchor hole.

18 Claims, 3 Drawing Sheets

U.S. PATENT DOCUMENTS

| | | | |
|---|---|---|---|
| 3,781,918 A | | 1/1974 | Mathys |
| 4,064,568 A | | 12/1977 | Grundei et al. |
| 4,231,120 A | | 11/1980 | Day |
| 4,245,359 A | | 1/1981 | Stuhmer |
| 4,261,062 A | | 4/1981 | Amstutz et al. |
| 4,375,703 A | | 3/1983 | Evans et al. |
| 4,725,280 A | * | 2/1988 | Laure ..................... 623/21.16 |
| 4,865,605 A | | 9/1989 | Dines et al. |
| 4,964,865 A | | 10/1990 | Burkhead et al. |
| 4,986,833 A | | 1/1991 | Worland |
| 4,990,161 A | | 2/1991 | Kampner |
| 5,032,132 A | * | 7/1991 | Matsen et al. ........... 623/19.11 |
| 5,080,673 A | | 1/1992 | Burkhead et al. |
| 5,108,441 A | | 4/1992 | McDowell |
| 5,108,446 A | * | 4/1992 | Wagner et al. ........... 623/22.28 |
| 5,489,310 A | | 2/1996 | Mikhail |
| 5,702,447 A | | 12/1997 | Walch et al. |
| 5,935,169 A | * | 8/1999 | Chan ..................... 623/23.48 |

FOREIGN PATENT DOCUMENTS

| | | |
|---|---|---|
| EP | 0 581 667 | 2/1994 |
| EP | 0 776 636 | 6/1997 |
| EP | 0 963 742 | 12/1999 |
| EP | 1 013 246 | 6/2000 |
| EP | 1 064 890 | 1/2001 |
| FR | 2 578 162 | 9/1986 |
| FR | 2 579 454 | 10/1986 |
| FR | 2 704 747 | 11/1994 |

OTHER PUBLICATIONS

Portion of an article from Clinical Orthopaedics and Related Research, No. 176, Jun. 1983, pp. 122-123.

The Roper-Day Total Shoulder Replacement, The Journal of Bone and Joint Surgery by B.A. Roper, J.M.H. Paterson, and W.H. Day, vol. 72-B, No. 4, Jul. 1990.

An All-Polythylene Cementless Tibial Component: A Five- to Nine-Year Follow-Ups Study by Kent Samuelson, M.D., and Lise Nelson, Clinical Orthopaedics and Related Reserch, No. 260, Nov. 1990.

Article entitled "Experimental Studies Leading to a Method for the Direct Fixation of a Polythelene Implant to Cancellous Bone" by M.A.R. Freeman, M.D., F.R.C.S., et al., 15 pages.

Article entitled "A Study of the Bone at the Site of Implantation of a Flanged Polyetheylene PEG in the Dog" by M.A.R. Freeman, M.D., F.R.C.S., et al., 5 pages.

* cited by examiner

METHOD FOR SECURING A GLENOID COMPONENT TO A SCAPULA

This application is a continuation of application Ser. No. 09/802,150, filed on Mar. 8, 2001 now U.S. Pat. No. 6,911,047, which in turn claims priority to U.S. Provisional Application Ser. No. 60/190,391, entitled "Apparatus and Method for Securing a Cementless Glenoid Component to a Glenoid Surface of a Scapula", filed on Mar. 17, 2000. The disclosure of each of the above-identified provisional and utility patent applications are hereby totally incorporated by reference in their entirety.

TECHNICAL FIELD OF THE INVENTION

The present invention relates generally to a glenoid component, and more particularly to an apparatus and method for securing a cementless glenoid component to a glenoid surface of a scapula.

BACKGROUND OF THE INVENTION

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component which provides a bearing surface for the head portion of the humeral component.

Glenoid components have heretofore been designed which include a number of plastic inserts coupled to metal backings. The metal backings are provided to secure the plastic inserts to the glenoid surface of the scapula. However, use of such two-piece glenoid components has a number of drawbacks associated therewith. For example, it is possible over the useful life of the glenoid component for the plastic inserts to separate from the metal backing thereby necessitating replacement of the glenoid component. In addition, over time wear of the plastic insert inherently occurs at the interface between plastic insert and the metal backing. It is possible for the plastic insert to wear to a degree which necessitates replacement of the glenoid component. It should be appreciated that in either case, such replacement of the glenoid component requires the patient to again be subjected to a surgical procedure and the subsequent recovery period associated therewith.

In response to the shortcomings associated with two-piece glenoid component designs, a number of one-piece glenoid components have heretofore been designed. In regard to such one-piece designs, a body portion, having a bearing surface defined therein for receiving the head of the humeral component, has a number of attachment pegs integrally formed therewith. The attachment pegs are advanced and thereafter secured into a corresponding number of holes which are drilled in the glenoid surface of the scapula by use of bone cement. An example of such a one-piece glenoid component that is designed to be secured to the scapula by use of bone cement is disclosed in U.S. Pat. No. 5,032,132 issued to Matsen, III et al.

As with the two-piece designs, certain one-piece glenoid components which have heretofore been designed have a number of drawbacks associated therewith. For example, recent studies have speculated that it may be desirable to secure artificial components to natural bone structures without the use of bone cement. Glenoid components which have been designed to be secured to the scapula by the use of bone cement generally cannot be secured to the scapula without use of the same.

What is needed therefore is a glenoid component which overcomes one or more of the above-mentioned drawbacks. What is particularly needed is a glenoid component which may be secured to the glenoid surface of the scapula without the use of bone cement.

SUMMARY OF THE INVENTION

In accordance with one embodiment of the present invention, there is provided a glenoid component for securement to a glenoid surface of a scapula so as to provide a bearing surface for a head portion of a humerus. The glenoid component includes a body portion having a first surface configured to contact the glenoid surface of the scapula and a second surface configured to receive the head portion of the humerus. The glenoid component also includes an anchor peg extending from the first surface of the body portion for penetrating the glenoid surface of the scapula so as to secure the body portion to the glenoid surface of the scapula. The anchor peg has a first end portion and a second end portion, with the first end portion of the anchor peg being secured to the first surface of the body portion, and the second end portion of the anchor peg having a number of fins secured thereto. The glenoid component also includes a first stabilizing peg extending from the first surface of the body portion for penetrating the glenoid surface of the scapula so as to prevent movement of the body portion relative to the glenoid surface of the scapula.

In accordance with another embodiment of the present invention, there is provided a method of securing a glenoid component to a glenoid surface of a scapula so as to provide a bearing surface for a head portion of a humerus. The glenoid component has (i) a body portion which has a first surface configured to contact the glenoid surface of the scapula and a second surface configured to receive the head portion of the humerus, (ii) an anchor peg extending from the first surface of the body portion, the anchor peg having a number of fins secured thereto, and (iii) a first stabilizing peg extending from the first surface of the body portion. The method includes the step of drilling an anchor hole and a first stabilizing hole in the glenoid surface of the scapula. The method also includes the step of advancing the anchor peg into the anchor hole so as to position the number of fins in the anchor hole. The method further includes the step of advancing the first stabilizing peg into the first stabilizing hole. The anchor peg advancing step and the first stabilizing peg advancing step are performed contemporaneously such that the first surface of the body portion is advanced into contact with the glenoid surface of the scapula.

In accordance with a further embodiment of the present invention, there is provided a glenoid component for securement to a glenoid surface of a scapula so as to provide a bearing surface for a head portion of a humerus. The glenoid component includes a body portion having a first surface configured to contact the glenoid surface of the scapula and a second surface configured to receive the head portion of the humerus. The glenoid component also includes an anchor peg having a shaft portion which extends outwardly from the first surface of the body portion for penetrating the glenoid surface of the scapula so as to secure the body portion to the glenoid surface of the scapula. The shaft portion of the anchor peg has a number of fins defined therein. The glenoid component further has a first stabilizing peg extending outwardly from the first surface of the body portion for penetrating the glenoid surface of the scapula so as to prevent movement of the body portion relative to the glenoid surface of the scapula. Each of the body portion, the anchor peg, the number of fins, and the stabilizing peg are integrally molded with one another.

In accordance with yet another embodiment of the present invention, there is provided a glenoid component for securement to a glenoid surface of a scapula so as to provide a bearing surface for a head portion of a humerus. The glenoid component includes a body portion having a first surface configured to contact the glenoid surface of the scapula, and a second surface configured to receive the head portion of the humerus. The glenoid component also includes an anchor peg extending from the first surface of the body portion for insertion into an anchor hole formed in the glenoid surface of the scapula so as to secure the body portion to the glenoid surface of the scapula. The anchor peg has an outwardly extending fin secured thereto. The fin is configured to deform upon insertion of the anchor peg into the anchor hole such that a removal force required to remove the anchor peg from the anchor hole is greater in magnitude than an insertion force required to insert the anchor peg into the anchor hole. The glenoid component also includes a first stabilizing peg extending from the first surface of the body portion for insertion into a stabilizing hole formed in the glenoid surface of the scapula so as to prevent movement of the body portion relative to the glenoid surface of the scapula.

In accordance with another embodiment of the present invention, there is provided a bearing component for securement to a natural bearing surface of a first bone so as to provide a bearing surface for a contact portion of a second bone. The bearing component includes a body portion having a first surface configured to contact the natural bearing surface of the first bone and a second surface configured to receive the contact portion of the second bone. The bearing component also includes an anchor peg extending from the first surface of the body portion for penetrating the natural bearing surface of the first bone so as to secure the body portion to the natural surface of the first bone. The anchor peg has a first end portion and a second end portion with the first end portion of the anchor peg being secured to the first surface of the body portion and the second end portion of the anchor peg having an outwardly extending fin secured thereto. The bearing component also includes a first stabilizing peg extending from the first surface of the body portion for penetrating the natural bearing surface of the first bone so as to prevent movement of the body portion relative to the natural bearing surface of the first bone.

It is therefore an object of the present invention to provide a new and useful glenoid component.

It is moreover an object of the present invention to provide an improved glenoid component.

It is a further object of the present invention to provide a new and useful method of securing a glenoid component to a glenoid surface of a scapula.

It is also an object of the present invention to provide an improved method of securing a glenoid component to a glenoid surface of a scapula.

It is yet another object of the present invention to provide a method of securing a glenoid component to a glenoid surface of a scapula which does not require the use of bone cement.

The above and other objects, features, and advantages of the present invention will become apparent from the following description and the attached drawings.

DETAILED DESCRIPTION OF THE INVENTION

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 1:
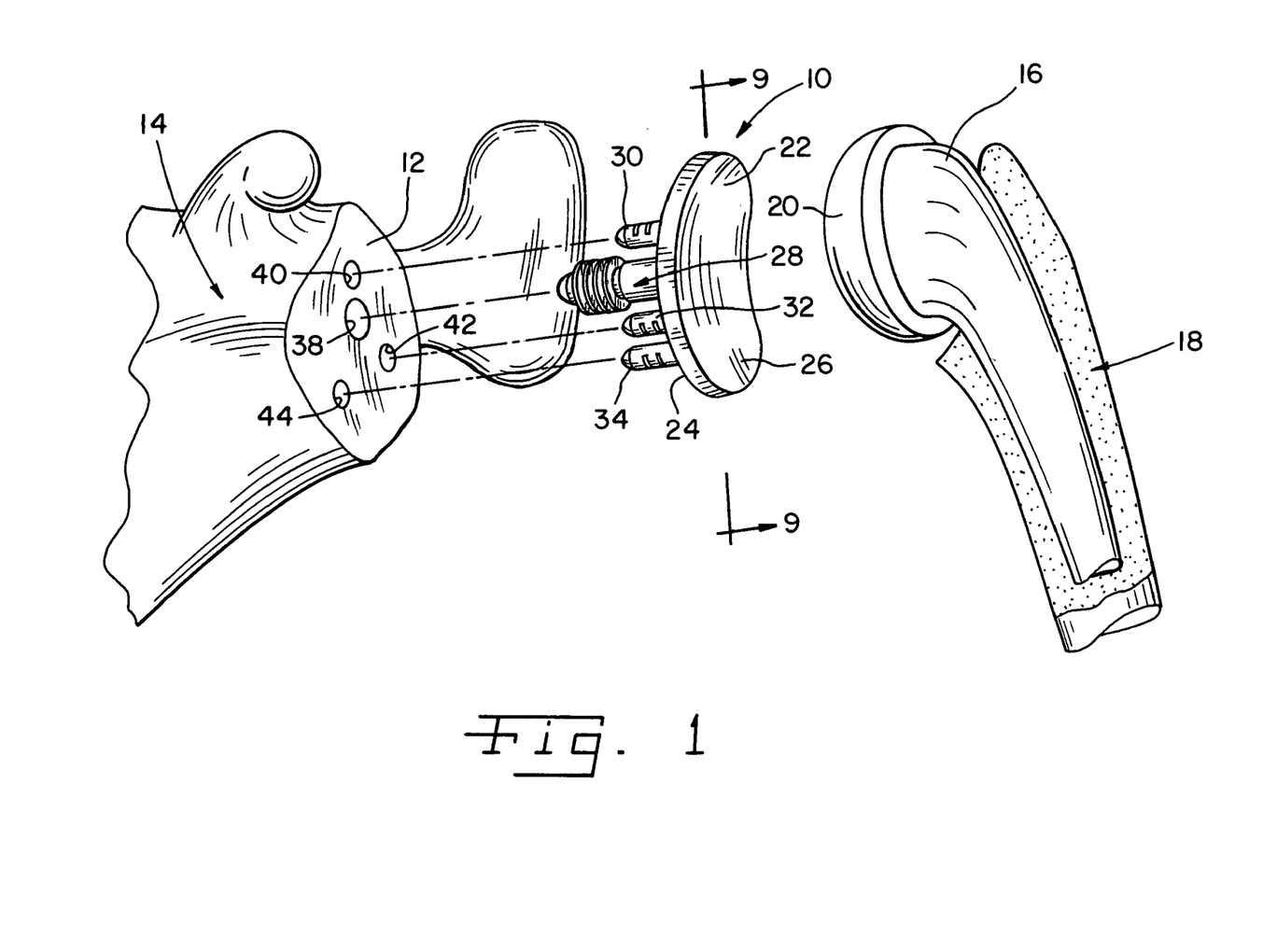
FIG. 1 is an exploded perspective view which shows a glenoid component which incorporates the features of the present invention therein positioned between a glenoid surface of a scapula and a humeral component.
Figure 2:
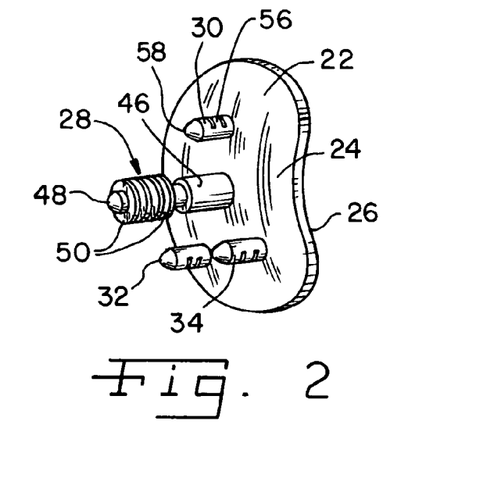
FIG. 2 is a perspective view of the glenoid component of FIG. 1.
Figure 3:
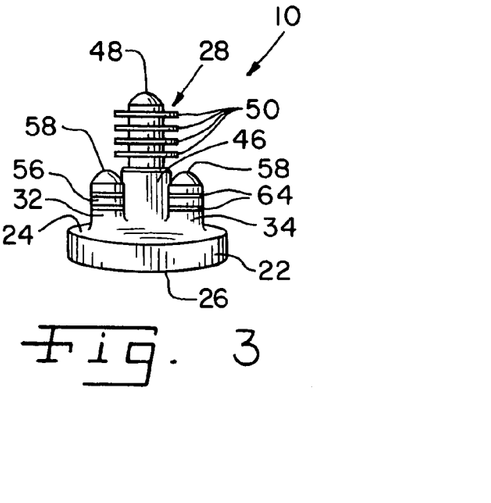
FIGS. 3–5 are elevational views of the glenoid component of FIG. 2.
Figure 4:
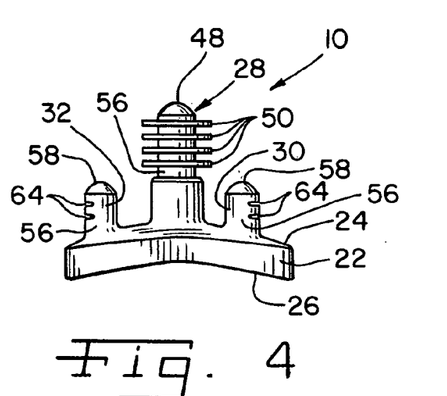

Referring now to FIG. 1, there is shown a glenoid component 10 located between a glenoid surface 12 of a scapula 14 and a humeral component 16. The humeral component 16 has been implanted or otherwise secured to a humerus 18. As shall be discussed below in greater detail, the glenoid component 10 is configured to be secured to the glenoid surface 12 of the scapula 14 without the use of bone cement in order to replace the natural glenoid surface 12 during a total shoulder replacement procedure. In such a manner, the glenoid component 10 functions as a bearing surface for receiving a head portion of the humerus 18 (i.e. a head portion 20 of the humeral component 16 implanted in the humerus 18).

As shown in FIGS. 1–8, the glenoid component 10 includes a body portion 22 having a first generally convex surface 24 and a second generally concave surface 26. The convex surface 24 is configured to abut or otherwise contact the glenoid surface 12 of the scapula 14 when the glenoid component 10 is secured thereto. The concave surface 26 of the body portion 22 provides a bearing surface for the head portion 20 of the humeral component 16 implanted into the humerus 18.

The glenoid component also includes an anchor peg 28 and a number of stabilizing pegs 30, 32, 34. The anchor peg 28 and the stabilizing pegs 30, 32, 34 are secured to the convex surface 24 of the body portion 22 and extend outwardly therefrom. As shown in FIG. 1, the anchor peg 28 is received into an anchor hole 38 which is drilled or otherwise formed in the glenoid surface 12 of the scapula 14, whereas the stabilizing pegs 30, 32, 34 are received into a number of respective stabilizing holes 40, 42, 44 which are also drilled or otherwise formed in the glenoid surface 12 of the scapula 14.

Although it is contemplated that the anchor peg 28 and/or any one or all of the stabilizing pegs 30, 32, 34 may be embodied as separate components which are secured to the body portion 22, the anchor peg 28 and the stabilizing pegs 30, 32, 34 are preferably integrally formed with one another and the body portion 22. In one exemplary embodiment, the body portion 22, the anchor peg 28, and the stabilizing pegs 30, 32, 34 are integrally molded using a polymeric material such as polyethylene or ultra-high molecular weight polypropylene (UHMWPE).

Figure 5:
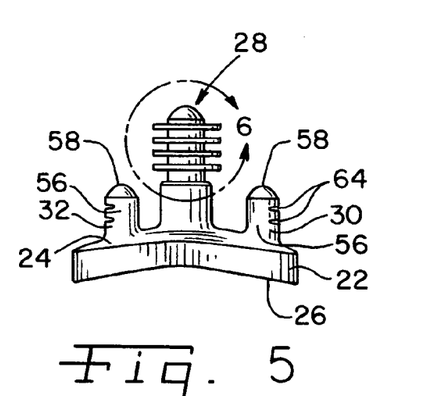
Figure 6:
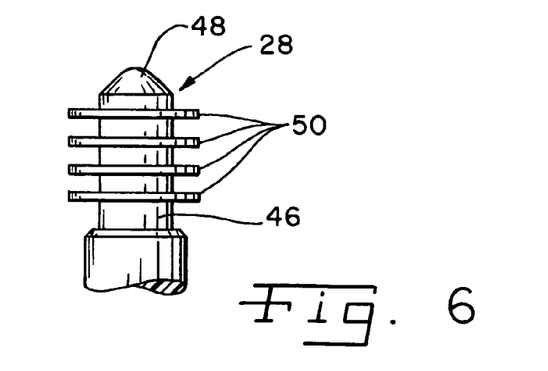
FIG. 6 is an enlarged view of a portion of FIG. 5 which is encircled and indicated as FIG. 6.

As shown best in FIGS. 5 and 6, the anchor peg 28 includes a beveled shaft portion 46 which is secured at its proximal end to the convex surface 24. The distal end portion of the shaft portion 46 has a conical tip 48 defined therein which is provided as a "lead in" to facilitate insertion of the anchor peg 28 into the anchor hole 38 drilled in the glenoid surface 12 of the scapula 14.

In addition to the conical tip 48, the distal end portion of the shaft portion 46 also has a number of fins 50 secured thereto. The fins 50 extend radially outwardly from the shaft portion 46 of the anchor peg 28 in a substantially perpendicular direction relative to the shaft portion 46 such that the outer diameter of each of the fins 50 is greater than the outer diameter of the shaft portion 46. Each of the fins 50 preferably extends continuously around the entire outer periphery of the shaft portion 46, although the fins 50 may alternatively be embodied as a series of individual flange sections which line substantially all of the outer periphery of the shaft portion 46.

Although the anchor peg 28 is herein shown in the figures to include four fins 50, it should be appreciated that the anchor peg 28 may be embodied to include any number of fins. For example, the anchor peg 28 may be embodied to include only a single (i.e. one) fin 50. In addition, although each of the fins 50 is herein shown in the figures to possess the same sized outer diameter, it should be appreciated that other fin configurations are also contemplated for use with the glenoid component 10 of the present invention. For example, the fins 50 may be provided in a tapered configuration in which the respective outer diameters of the fins 50 gradually increases from the distal end of the shaft portion 46 to the proximal end portion of the shaft portion (i.e. the fin positioned on the distal end of the shaft portion 46 has a smaller diameter relative to the fin positioned on the proximal end of the shaft portion 46). In such a configuration, the anchor hole 38 drilled in the scapula 14 would be drilled in a similarly tapered manner so as to provide a corresponding sidewall configuration for engagement by the fins 50.

Although it is contemplated that the fins 50 may be embodied as separate components which are secured to the shaft portion 46 of the anchor peg 28, the fins 50 are preferably integrally formed with the shaft portion 46 of the anchor peg 28. Consistent with as described above, in one exemplary embodiment, the fins 50 are integrally molded with the shaft portion 46 of the anchor peg 28 (and hence also integrally molded with the body portion 22 and the stabilizing pegs 30, 32, 34 of the glenoid component 10) using a polymeric material such as polyethylene or ultra-high molecular weight polypropylene (UHMWPE).

Figure 9:
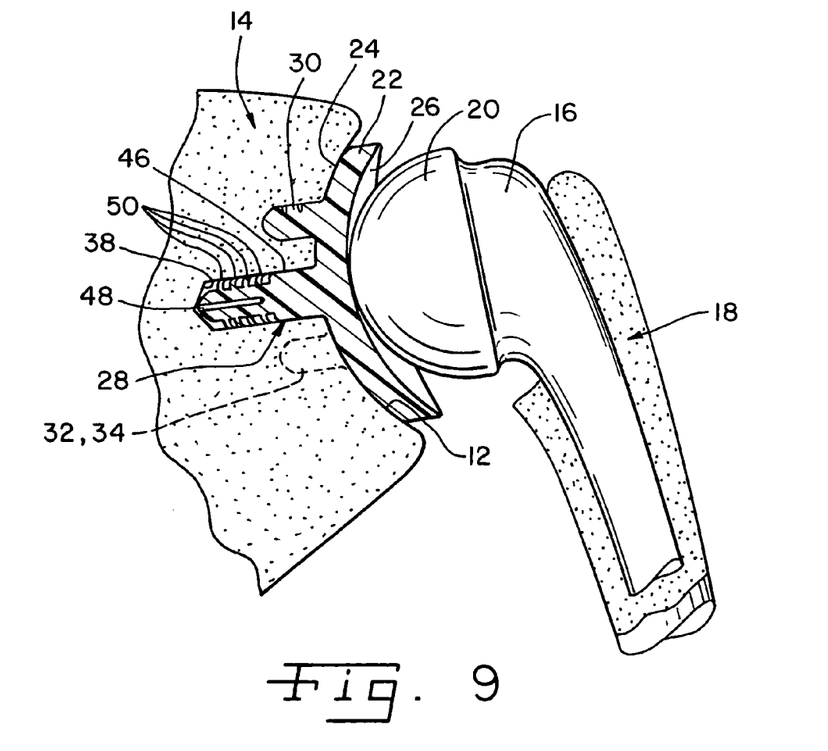
FIG. 9 is a cross sectional view taken along the line 9—9 of FIG. 1 as viewed in the direction of the arrows, note that the fins of the glenoid component are not shown in cross section for clarity of description.

As shown in FIG. 9, the fins 50 are configured to curl, bend, or otherwise deform when the anchor peg 28 is inserted into the anchor hole 38. This is caused when the fins 50 are advanced into the anchor hole 38 since it is drilled so as to have a diameter which is slightly larger than the diameter of the shaft portion 46 of the anchor peg 28, yet smaller than the outer diameter of the fins 50 thereby causing deformation of the fins 50 upon contact with the sidewalls of the anchor hole 38 as the fins 50 are "forced" into the anchor hole 38. Such deformation of the fins 50 allows the fins 50 to function as upwardly turned "barbs" which secure the glenoid component 10 to the scapula 14 by providing resistance to removal or "pull out" of the anchor peg 28 from the anchor hole 38 much in the same way that the threads of a screw provide resistance to pull out of the screw from the material into which it is driven. In addition, over a period of time subsequent to securement of the glenoid component 10 to the scapula 14, bone tissue or other types of tissue will grow into the spaces between the fins 50 thereby providing further resistance to pull out of the anchor peg 28 from the anchor hole 38.

Moreover, the fins 50 of the present invention are configured in a manner which provides numerous advantages over heretofore designed anchoring structures. For example, the fins 50 are configured to be relatively thin in design and possess a relatively large outer diameter thereby providing for a relatively large amount of deformation or "curling" which in turn creates a large amount of anchoring force when the anchor peg 28 is inserted into the anchor hole 38. In one exemplary embodiment, each of the fins 50 has a nominal thickness of 0.023 inch with a distance of 0.052 inch between adjacent fins. Moreover, in such an exemplary embodiment, the fins 50 have an outer diameter of 0.346 inch and extend outwardly from a shaft portion 46 which has a diameter of 0.188 inch.

Such a configuration of the fins 50 as described above eliminates the need for the use of bone cement to secure the anchor peg 28 to the glenoid surface 12 of the scapula 14 thereby reducing the complexity of a typical total shoulder replacement procedure along with eliminating any potential shortcomings associated with the use of bone cement. In particular, the above-described configuration of the fins 50 provides a glenoid component 10 which "locks" into place upon insertion into the anchor hole 38 drilled in the scapula 14. More specifically, preliminary laboratory tests have indicated that when inserted into a test material such as white pine wood, the removal force required to remove the glenoid component 10 is over twice as large in magnitude as the insertion force required to press fit the glenoid component 10 into the test material. The creation of such a relatively large removal force facilitates the use of the glenoid component 10 without the use of bone cement.

The stabilizing pegs 30, 32, 34 are provided to prevent rotation or other types of movement of the body portion 22 of the glenoid component 10 relative to the scapula 14 once the glenoid component 10 has been secured to the glenoid surface 12. Each of the stabilizing pegs 30, 32, 34 includes a cylindrical shaft portion 56 which is secured at its proximal end to the convex surface 24 of the body portion 22. The distal end of each of the shaft portions 56 has a conical tip 58 defined therein which, similarly to as described above in regard to the anchor peg 28, functions as a "lead in" to facilitate insertion of the stabilizing pegs 30, 32, 34 into their respective stabilizing holes 40, 42, 44 drilled in the glenoid surface 12 of the scapula 14.

Figure 7:
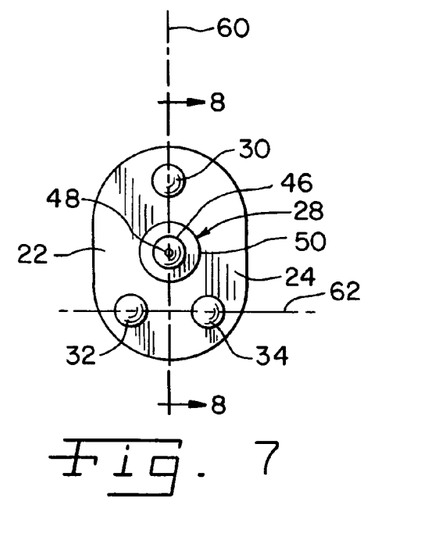
FIG. 7 is a plan view of the glenoid component of FIG. 2.
Figure 8:
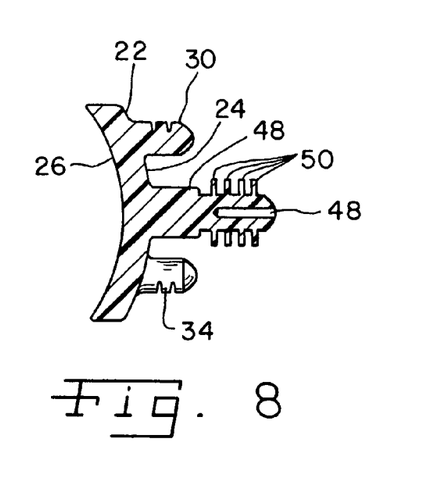
FIG. 8 is a cross sectional view taken along the line 8—8 of FIG. 7, as viewed in the direction of the arrows.

The stabilizing pegs 30, 32, 34 may be arranged in any orientation on the convex side 24 of the body portion 22 which fits the needs of a given glenoid component 10. For example, as shown best in FIG. 7, the stabilizing peg 30 may be spaced apart from the anchor peg 28 in a direction which is substantially opposite from the direction in which the stabilizing pegs 32, 34 are spaced apart from the anchor peg 28. Moreover, one arrangement of the stabilizing pegs 30, 32, 34 which has been found to be particularly useful for preventing rotation or other types of movement of the glenoid component 10 relative to the scapula 14 is an arrangement shown in FIG. 7 in which a first pair of pegs (i.e. the anchor peg 28 and the stabilizing peg 30) are positioned in a normal relationship with a second pair of pegs (i.e. the stabilizing pegs 32, 34). In particular, as shown in FIG. 7, the anchor peg 28 and the stabilizing peg 30 are aligned with respect to one another along a first imaginary line 60, whereas the stabilizing peg 32 and the stabilizing peg 34 are aligned with respect to one another along a second imaginary line 62. The imaginary line 60 is normal or otherwise substantially perpendicular to the imaginary line 62.

In addition, it should be appreciated that any number of stabilizing pegs may be utilized to fit the needs of a given glenoid component 10. In particular, although the glenoid component 10 is described herein as having three stabilizing pegs, and has significant advantages thereby in the present invention, it should be appreciated that the glenoid component 10 may be alternatively embodied to include any number of stabilizing pegs. For example, the glenoid component 10 may be embodied to include only a single (i.e. one) stabilizing peg.

Moreover, as shown in FIGS. 3–5 and 8, the stabilizing pegs 30, 32, 34 may alternatively be configured to have a number of serrations 64 defined therein. The serrations 64 may be utilized in a similar manner as the fins 50 of the anchor peg 28 in that over a period of time subsequent to securement of the glenoid component 10 to the scapula 14, bone tissue or other types of tissue will grow into the serrations 64 thereby providing resistance to pull out of the glenoid component 10 from its secured position on the glenoid surface 12 of the scapula 14. Moreover, if a particular surgeon or procedure requires (or simply desires) the use bone cement in the stabilizing holes 40, 42, 44 due to, for example, governmental regulation or the like, the serrations 64 may be utilized to receive a portion of the bone cement in order to increase the area of contact between the bone cement and the stabilizing pegs 30, 32, 34 thereby increasing the bond between the stabilizing pegs 30, 32, 34 and the walls of the stabilizing holes 40, 42, 44.

Hence, the glenoid component 10 may be secured to the glenoid surface 12 of the scapula 14 in a number of different manners. In a first or "cementless" manner, each of the anchor peg 28 and the stabilizing pegs 30, 32, 34 is press fit or otherwise interference fit into their respective holes 38, 40, 42, 44 without the use of bone cement. In a second or "cemented" manner, the anchor peg 28 is press fit or otherwise interference fit into the anchor hole 38 in the same manner as described above; however, the stabilizing pegs 30, 32, 34 are clearance fit into their respective stabilizing holes 40, 42, 44 with the use of bone cement. Such multiple uses of the glenoid component 10 of the present invention provides flexibility in regard to its use thereby fulfilling the needs of a given surgeon or shoulder replacement procedure.

Operation of the Present Invention

In operation, the glenoid component 10 of the present invention is utilized in the performance of a total shoulder replacement procedure in order to provide an artificial bearing surface for the head portion of the humerus without the use of bone cement. In particular, the anchor hole 38 and the stabilizing holes 40, 42, 44 are first drilled or otherwise formed in the glenoid surface 12 of the scapula 14 by use of a suitable drilling tool (not shown). It should be appreciated that a drill guide or pattern (not shown) may be utilized to properly position and align the holes 38, 40, 42, 44 on the glenoid surface 12 of the scapula 14.

Once the holes 38, 40, 42, 44 have been drilled in the glenoid surface 12 of the scapula 14, the glenoid component 10 is secured to the scapula 14. In particular, the glenoid component 10 is oriented such that the anchor peg 28 and the stabilizing pegs 30, 32, 34 are pointed in the general direction of the glenoid surface 12 of the scapula 14. Thereafter, the glenoid component 10 is advanced toward the glenoid surface 12 such that the anchor peg 28 and each of the stabilizing pegs 30, 32, 34, are contemporaneously advanced into the anchor hole 38 and the stabilizing holes 40, 42, 44, respectively.

As described above, the fins 50 are configured to curl, bend, or otherwise deform when the anchor peg 28 is inserted into the anchor hole 38 so as to allow the fins 50 to function as "barbs" which secure the glenoid component 10 to the scapula 14 by providing resistance to pull out of the anchor peg 28 from the anchor hole 38 much in the same way that the threads of a screw provide resistance to pull out of the screw from the material into which it is driven. In addition, as described above, over time a period of time subsequent to securement of the glenoid component 10 to the scapula 14, bone tissue or other types of tissue will grow into the spaces between the fins 50 thereby providing further resistance to pull out of the anchor peg 28 from the anchor hole 38.

Hence, insertion of the anchor peg 28 into the anchor hole 38 anchors or otherwise retains the body portion 22 of the glenoid component 10 into contact with the glenoid surface 12 of the scapula 14. Moreover, insertion of the stabilizing pegs 30, 32, 34 into the stabilizing holes 40, 42, 44 in the manner described above prevents rotation or other types of movement of the body portion 22 of the glenoid component 10 relative to the glenoid surface 12 of the scapula 14.

Once the glenoid component 10 has been secured to the glenoid surface 12 of the scapula 14 in the manner described, the concave surface 26 of the body portion 22 of the glenoid component 10 provides a bearing surface for receiving the head portion 20 of the humeral component 16 implanted in the humerus 18. In such a manner, the concave surface 26 of the body portion 22 functions as a suitable artificial replacement for the natural glenoid surface 12 of the scapula 14.

Hence, as described herein, the glenoid component 10 of the present invention provides numerous advantages over heretofore designed glenoid components. For example, the glenoid component 10 is configured to be secured to the glenoid surface 12 of the scapula 14 without the use of bone cement. Moreover, the glenoid component 10 of the present invention is preferably provided as a one-piece, integrally molded component thereby overcoming many of the drawbacks associated with heretofore designed multiple-piece designs.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the glenoid component described herein. It will be noted that alternative embodiments of the glenoid component of the present invention may not include all of the features described yet still benefit from at least some of the advantages of such features. Those of ordinary skill in the art may readily devise their own implementations of a glenoid component that incorporate one or more of the features of the present invention and fall within the spirit and scope of the present invention as defined by the appended claims.

For example, the embodiment of one bearing component in accordance with the concepts of the present invention has herein been described in regard to the glenoid component 10. However, it should be appreciated that the concepts of the present invention may also be incorporated into an acetabular, patellar, femoral, humeral, tibial, ulnar, radial, wrist, and/or ankle component for a prosthetic joint assembly.

What is claimed is:

1. A medical procedure, comprising:
   providing a prosthesis which includes (i) a body portion having a rear surface and a bearing surface, and (ii) an anchor peg including a shaft extending from said rear surface of said body portion, wherein said shaft includes a first shaft portion and a second shaft portion, and wherein said anchor peg includes a plurality of outwardly extending fins secured to said first shaft portion, and further wherein said plurality of outwardly extending fins each possesses a first diameter;
   creating an anchor hole in a natural bone so as to define an anchor hole sidewall, said anchor hole possessing a second diameter which is less than said first diameter; and
   positioning said anchor peg within said anchor hole so that:
   (A) each of said plurality of outwardly extending fins deforms so as to possess (i) a concave side which faces an open end of said anchor hole, and (ii) a convex side that faces a closed end of said anchor hole, and
   (B) said second shaft portion of said shaft of said anchor peg is positioned in contact with said anchor hole sidewall,
   wherein said first shaft portion of said shaft of said anchor peg possesses a third diameter,
   wherein said second shaft portion of said shaft of said anchor peg possesses a fourth diameter, and
   wherein said fourth diameter is greater than said third diameter.

2. The medical procedure of claim 1, wherein said prosthesis further includes at least one stabilizing peg extending from said rear surface of said body portion, further comprising the step of:
   creating a stabilizing hole in said natural bone at a location spaced apart from said anchor hole; and
   positioning said at least one stabilizing peg within said stabilizing hole.

3. The medical procedure of claim 2, wherein said body portion, said anchor peg, and said at least one stabilizing peg are integrally molded together to form a one-piece component.

4. The medical procedure of claim 1, wherein said body portion and said anchor peg are integrally molded with one another using a polymeric material.

5. The medical procedure of claim 4, wherein said polymeric material includes polyethylene.

6. The medical procedure of claim 1, wherein:
   said prosthesis is a glenoid component, and
   said natural bone is a scapula.

7. The medical procedure of claim 1, further comprising the step of positioning a humeral head in contact with said bearing surface of said body portion of said prosthesis.

8. The medical procedure of claim 1, wherein all fins of said anchor peg extend from said first shaft portion.

9. The medical procedure of claim 1, wherein each of said plurality of outwardly extending fins of said anchor peg are spaced apart from said second shaft portion.

10. A medical procedure, comprising:
    providing a prosthesis which includes (i) a body portion having a rear surface and a bearing surface, and (ii) an anchor peg including a shaft extending from said rear surface of said body portion, wherein said shaft includes a first shaft portion and a second shaft portion, and wherein said anchor peg includes a plurality of outwardly extending fins secured to said first shaft portion,
    creating an anchor hole in a natural bone so as to define an anchor hole sidewall; and
    positioning said anchor peg within said anchor hole so that:
    (A) each of said plurality of outwardly extending fins deforms so as to possess (i) a concave side which faces an open end of said anchor hole, and (ii) a convex side that faces a closed end of said anchor hole, and
    (B) said second shaft portion of said shaft of said anchor peg is positioned in contact with said anchor hole sidewall,
    wherein said first shaft portion of said shaft of said anchor peg possesses a first diameter,
    wherein said second shaft portion of said shaft of said anchor peg possesses a second diameter, and
    wherein said second diameter is greater than said first diameter.

11. The medical procedure of claim 10, wherein said prosthesis further includes at least one stabilizing peg extending from said rear surface of said body portion, further comprising the step of:
    creating a stabilizing hole in said natural bone at a location spaced apart from said anchor hole; and
    positioning said at least one stabilizing peg within said stabilizing hole.

12. The medical procedure of claim 11, wherein said body portion, said anchor peg, and said at least one stabilizing peg are integrally molded together to form a one-piece component.

13. The medical procedure of claim 10, wherein said body portion and said anchor peg are integrally molded with one another using a polymeric material.

14. The medical procedure of claim 10, wherein:
    said prosthesis is a glenoid component, and said natural bone is a scapula.

15. The medical procedure of claim 10, further comprising the step of positioning a humeral head in contact with said bearing surface of said body portion of said prosthesis.

16. The medical procedure of claim 10, wherein said second shaft portion of said shaft of said anchor peg is cylindrically shaped.

17. The medical procedure of claim 10, wherein all fins of said anchor peg extend from said first shaft portion.

18. The medical procedure of claim 10, wherein each of said plurality of outwardly extending fins of said anchor peg are spaced apart from said second shaft portion.

* * * * *

UNITED STATES PATENT AND TRADEMARK OFFICE
CERTIFICATE OF CORRECTION

| | | |
|---|---|---|
| PATENT NO. | : 7,160,328 B2 | Page 1 of 1 |
| APPLICATION NO. | : 11/129966 | |
| DATED | : January 9, 2007 | |
| INVENTOR(S) | : Rockwood, Jr. et al. | |

It is certified that error appears in the above-identified patent and that said Letters Patent is hereby corrected as shown below:

On the title page (73) delete

"DePuty Products, Inc., Warsaw, IN (US)"

Change to read:

--DePuy Products, Inc., Warsaw, IN (US)--.

Signed and Sealed this

Ninth Day of October, 2007

JON W. DUDAS
*Director of the United States Patent and Trademark Office*